United States Patent
De Haan

(10) Patent No.: US 10,575,764 B2
(45) Date of Patent: Mar. 3, 2020

(54) SYSTEM AND METHOD FOR EXTRACTING PHYSIOLOGICAL INFORMATION FROM REMOTELY DETECTED ELECTROMAGNETIC RADIATION

(71) Applicant: KONINKLIJKE PHILIPS N.V., Eindhoven (NL)

(72) Inventor: Gerard De Haan, Helmond (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 311 days.

(21) Appl. No.: 15/696,813

(22) Filed: Sep. 6, 2017

(65) Prior Publication Data
US 2017/0360340 A1 Dec. 21, 2017

Related U.S. Application Data

(63) Continuation of application No. 14/907,592, filed as application No. PCT/EP2014/065997 on Jul. 25, 2014, now abandoned.
(Continued)

(30) Foreign Application Priority Data

Jul. 8, 2013 (EP) ..................................... 13179563

(51) Int. Cl.
*A61B 5/1455* (2006.01)
*A61B 5/00* (2006.01)
(Continued)

(52) U.S. Cl.
CPC ........ *A61B 5/14552* (2013.01); *A61B 5/0059* (2013.01); *A61B 5/04* (2013.01);
(Continued)

(58) Field of Classification Search
CPC .............. A61B 5/0077; A61B 5/02416; A61B 5/14551; A61B 5/742; A61B 2576/00;
(Continued)

(56) References Cited

U.S. PATENT DOCUMENTS 4,029,085 A   6/1977   Dewitt et al.
5,353,790 A   10/1994  Jacques et al.
(Continued)

FOREIGN PATENT DOCUMENTS

CN   102861379 A   1/2013
DE   19741982 A1   10/1998
(Continued)

OTHER PUBLICATIONS

Verkruysse et al, "Remote Plethysmographic Imaging Using Ambient Light", Optics Express, vol. 16, No. 26, 2008, pp. 21434-21445.
(Continued)

*Primary Examiner* — Deborah L Malamud

(57) ABSTRACT

The present disclosure relates to a device and a method for extracting physiological information indicative of at least one health symptom from remotely detected electromagnetic radiation. The device comprises an interface for receiving a data stream comprising remotely detected image data representing an observed region comprising at least one subject of interest, wherein the image data comprises wavelength-dependent image information, wherein the wavelength-dependent image information is composed of at least two color channels representative of respective wavelength portions; an image processor for detecting channel signal strength information for at least two of the at least two color channels; and a data comparison unit for comparing detected channel signal strengths with respective reference values.

18 Claims, 8 Drawing Sheets

Related U.S. Application Data

(60) Provisional application No. 61/862,565, filed on Aug. 6, 2013.

(51) Int. Cl.
*A61B 5/04* (2006.01)
*A61B 5/145* (2006.01)
*A61N 5/10* (2006.01)

(52) U.S. Cl.
CPC ........ *A61B 5/1455* (2013.01); *A61B 5/14546* (2013.01); *A61B 5/14551* (2013.01); *A61N 5/10* (2013.01); *A61B 5/0077* (2013.01); *A61B 2503/045* (2013.01)

(58) Field of Classification Search
CPC ... A61B 5/0002; A61B 1/0005; A61B 90/361; A61B 2090/364; A61B 2034/2065; A61B 2090/397; A61B 5/0064; A61B 5/0082; A61B 5/02427; A61B 5/0295; A61B 5/486; A61B 5/743; A61B 6/5229; A61B 6/5247; A61B 5/0035; A61B 5/04; A61B 5/1032; A61B 5/4869; A61B 5/74; A61B 5/7425; A61B 5/7475; G06K 9/2018; G06K 2209/05; G06K 9/624; A61N 5/0613; G06F 19/3418; G06F 19/321; G06F 19/345; G06T 7/0012; G06T 2207/30076; G06T 2200/24

See application file for complete search history.

(56) References Cited

U.S. PATENT DOCUMENTS 6,064,898 A 5/2000 Aldrich
6,882,873 B2 4/2005 Samuels et al.
2008/0275349 A1 11/2008 Halperin et al.
2011/0157340 A1 6/2011 Yamazaki et al.
2011/0301441 A1 12/2011 Bandic et al.
2012/0195486 A1 8/2012 Kirenko
2012/0197137 A1 8/2012 Jeanne et al.
2013/0057865 A1 3/2013 Meijer et al.

FOREIGN PATENT DOCUMENTS

EP 747002 A1 12/1996
WO 2011148280 A1 12/2011
WO 2013038326 A1 3/2013

OTHER PUBLICATIONS

Alla et al, "Signal Processing System to Extract Serum Bilirubin Concentration From Diffuse Reflectance Spectrum of Human Skin", 31st Annual International Conference of the IEEE EMBS, 2009, pp. 1290-1293.

Lascari, "Carotenemia. A Review", Clinical Pediatrics, vol. 20, No. 1, pp. 25-29.

Rubins et al, "The Blood Perfusion Mapping in the Human Skin by Photoplethysmography Imaging", Medicon, IFMBE Proceedings 29, 2010, pp. 304-306.

Chandrasekaran, "Measuring Vital Signs Using Smart Phones", Thesis Prepared for the Degree of Master of Science, 2010, pp. 1-146.

Poh et al, "Non-contact, Automated Cardiac Pulse Measurements Using Video Imaging and Blind Source Separation", Optics Express, vol. 18, No. 10, 2010, pp. 10762-10744.

Vogel, "Noninvasive Imaging Techniques as a Quantitative Analysis of Kaposi's Sarcoma Skin Lesions", Dissertation Submitted to the Faculty of the Graduate School of the University of Maryland, 2007, pp. 1-122.

Lewandowska et al, "Measuring Pulse Rate With a Webcam—A Non-contact Method for Evaluating Cardiac Activity", Proceedings of the Federated Conference on Computer Science and Information Systems, 2011, pp. 405-410.

SYSTEM AND METHOD FOR EXTRACTING PHYSIOLOGICAL INFORMATION FROM REMOTELY DETECTED ELECTROMAGNETIC RADIATION

CROSS-REFERENCE TO PRIOR APPLICATIONS

This application is a divisional application of U.S. National Phase application under 35 U.S.C. § 371, Ser. No. 14/907,592, filed on Jan. 26, 2016, which claims the benefit of International Application Serial No. PCT/EP2014/065997, filed on Jul. 25, 2014, which claims the benefit of U.S. Application Ser. No. 61/862,565, filed on Aug. 6, 2013 and European Application No. 13179563.5, filed on Aug. 7, 2013. These applications are hereby incorporated by reference herein.

FIELD OF THE INVENTION

The present disclosure relates to a system and a method for extracting physiological information indicative of at least one health symptom from remotely detected electromagnetic radiation. More particularly, the present disclosure may contribute in analyzing vital signs information indicative of vital parameters, physiological parameters or, more generally, health parameters. The electromagnetic radiation may be considered as radiation in the visible wavelength band re-emitted by a subject of interest. As used herein, visible radiation may relate to radiation in a particular wavelength range which is visible to a human eye, or, at least to a sensing device. Even more specifically, the present disclosure may relate to (visible) image capturing and processing systems and corresponding methods for detecting and monitoring vital parameters and/or symptom-indicative information which may be applied, for instance, in the field of remote monitoring, such as remote photoplethysmographic monitoring.

The disclosure further relates to a corresponding computer readable non-transitory medium

BACKGROUND OF THE INVENTION

WO 2011/148280 A1 discloses a device and a method for measuring an analyte of a subject, the device comprising:
a number of narrow band light sources, each narrow band light source being structured to emit a spectrum of light covering a number of wavelengths; and
a number of detector assemblies configured to receive light reflected from a subject, each of the detector assemblies including a filter and a photodetector, each filter being structured to transmit a main transmission band and one or more transmission side bands, wherein for each narrow band light source the spectrum thereof includes one or more wavelengths that fall within the one or more transmission sidebands of any of the filters.

The document further discloses several refinements of the method and the device. For instance, it is suggested to utilize respective light emitting diodes (LED) as the narrow band light sources. Furthermore, it is envisaged to integrate both the narrow band light sources and the detector assemblies into a single system and to position the integrated system closely to a measurement surface of a subject to be monitored. Eventually, the document seeks after a determination of transcutaneous bilirubin and, based thereon, an estimation of a serum bilirubin level.

While basically avoiding blood sampling for assessing a subject's physiological condition or health condition, the device and method of WO 2011/148280 A1 may still be considered as an obtrusive approach for subject monitoring or patient monitoring, at least to a certain extent. The teaching of WO 2011/148280 A1 pertains to the field of contact measurement and/or contact monitoring basically requiring to closely attach sensors, emitters, transducers and further equipment to the monitored subject. This may be experienced as being considerably unpleasant. Particularly this holds true in the field of neonatal monitoring or, more generally, infant monitoring.

Recently, remote digital image-based monitoring systems for obtaining patient information or, physiological information of living beings in general, have been described and demonstrated.

As used herein, the term "remotely detected electromagnetic radiation" may refer to radiation components which are sent to a subject of interest from a radiation source (such as a remotely positioned light source) and "reflected" by a skin portion or dermal portion of the subject of interest. Also the subject's tissue beneath the skin's top surface plays a role in the reflection, deflection and/or absorption of incident radiation. Since reflection mechanisms in the subject's skin are rather complex and multi-dependent on factors such as wavelengths, penetration, depth, skin composition, vascular system structure, and further influencing parameters, terms such as "emitted", "transmitted" and "reflected" shall not be understood in a limited way. Typically, a portion of incident radiation may be reflected at the skin's (upper) surface. Furthermore, a portion of incident radiation may penetrate the skin and pass through skin layers. Eventually, at least a portion of the incident penetrating radiation may be absorbed in the skin, while at least another portion of incident penetrating radiation may be scattered in the skin (rather than reflected at the skin's surface). Consequently, radiation components representing the subject of interest which can be captured by a sensor, particularly an image sensor, can be referred to a re-emitted radiation in this context.

For remote monitoring and measurement approaches, the use of cameras has been demonstrated. Cameras may particularly involve video cameras capable of capturing sequences of image frames. Preferably, cameras capable of capturing visible light can be used. These cameras may comprise a certain responsibility (or: sensitivity) characteristic which covers at least a considerable portion of a visible light range of the electromagnetic spectrum. As used herein, visible light shall be understood as part of the electromagnetic spectrum which can be sensed by the human eye without further technical aids.

Remote subject monitoring, e.g., patient monitoring, is considered beneficial since in this way unobtrusive non-contact measurements can be conducted. By contrast, non-remote (contact) measurements typically require sensors and even markers to be applied to a skin portion of interest of the subject to be monitored. In many cases, this is considered unpleasant, particularly for long-term monitoring.

It would be therefore beneficial to provide for a system and a method for remote monitoring which further contribute to overcoming the need of obtrusive (contact) measurements.

Photoplethysmography (PPG) is an optical measurement technique that evaluates a time-variant change of light reflectance or transmission of an area or volume of interest. PPG is based on the principle that blood absorbs light stronger than surrounding tissue, so variations in blood volume with every heartbeat affect transmission or reflectance correspondingly. Besides information about the heart rate, a PPG waveform can comprise information at reputable further physiological phenomena such as respiration.

In this connection, Verkruysse et al., "Remote plethysmographic imaging using ambient light", Optics Express, 16(26), 22 Dec. 2008, pp. 21434-21445 demonstrates that photoplethysmographic signals can be measured remotely with normal ambient light and rather conventional consumer level video cameras.

Conventional PPG devices, such as pulse oximeters for measuring the heart rate and the (arterial) blood oxygen saturation (also called SpO2) of a subject are to be attached to the skin of the subject, for instance to a finger tip, earlobe or forehead. Therefore, they are referred to as "contact" PPG devices.

SUMMARY OF THE INVENTION

It is therefore an object of the present disclosure to seek for additional applications of PPG systems and corresponding methods. Particularly, it is an object of the present disclosure to provide a system and a method for extracting physiological information being capable of assisting in assessing health symptoms and contributing to diagnostic routines.

More particularly, it would be advantageous to provide a device and a corresponding method being capable of adequately processing remote PPG information without requiring multiple signal transformation steps. In other words, it would be beneficial to provide a method and a system for extracting physiological information that are particularly adapted to remotely detected image data which generally may comprise enormous disturbances and noise-affected portions.

In a first aspect of the present disclosure a system for extracting physiological information indicative of at least one health symptom from remotely detected electromagnetic radiation is presented, the system comprising:

an image sensor that remotely records image data, the image sensor comprising a responsivity adapted to capture electromagnetic radiation in at least two wavelength portions;

an interface that receives a data stream comprising the remotely detected image data representing an observed region comprising at least one subject of interest, wherein the image data comprises wavelength-dependent image information, wherein the wavelength-dependent image information is composed of at least two color channels representative of respective wavelength portions, the at least two color channels corresponding to the at least two wavelength portions captured by the image sensor;

an image processor that detects channel signal strength information for at least two of the at least two color channels;

a data comparison unit that compares detected channel signal strengths with respective reference values; and a symptom analyzer that derives blood composition-indicative information from a comparison of actual relative channel signal strengths with the reference values.

In a second aspect of the present disclosure a photoplethysmographic system for extracting physiological information indicative of at least one health symptom from remotely detected electromagnetic radiation is presented, the system comprising:

an interface that receives a data stream comprising remotely detected image data representing an observed region comprising a skin portion of at least one subject of interest, wherein the image data comprises wavelength-dependent image information, wherein the wavelength-dependent image information is composed of at least two color channels representative of respective wavelength portions;

an image processor that detects channel signal strength information for at least two of the at least two color channels; and a data comparison unit that compares detected channel signal strengths with respective reference values.

The present disclosure is based on the insight that several (health) symptoms occurring in a subject of interest, such as a patient or, more generally, a living being or a human being, typically involve a corresponding characteristic change of reflection and/or absorption properties at the subject's skin or in the subject's tissue or circulating blood. Consequently, upon monitoring the subject of interest and generating channel-based (color) image information, slight minute changes of color strengths or relative color strengths in at least one of the at least two channels may be highly indicative of respective health conditions or symptoms.

Particularly, the system may focus on relative channel signals strength information. Typically, the received data stream may comprise a PPG signal having a stable DC component and a relatively small pulsatile component (AC-portion) which may be attributed to the (blood) circulatory system in the subject. Blood pulsation causes slight minute color changes in the subject's tissue and/or the skin which may be detected upon monitoring and capturing respective image information. In other words, a signal representing the pulsatile component of the at least two color channels may be presented in a vector space by an index element (or: a vector) having a defined length and orientation attributable to actual relative signals strength values in each of the at least two color channels. Due to the blood pulsation, such an index element or vector may undergo a more or less periodic "reciprocating" motion between two end positions in the vector space. The path or curve of the reciprocating motion of the index element or vector may be used as an indicator for the presence of characteristic health symptoms. As used herein the term "relative signal strength" may relate to signal strength of an AC signal portion with respect to the (relatively constant or mean) DC signal portion of the same color channel. Consequently, an "absolute signal strength" may relate to an absolute signal strength of a signal incorporating the "constant" DC and the "pulsating" AC portion. The disclosure makes use of the fact that several specific symptoms may involve a characteristic variation in the pulsatile (AC) signal of at least one of the color channels with respect to at least one of the remaining color channels. Given that reference values (for instance, representing a healthy subject) for this reciprocating path or, more generally, for the channel signal strengths for at least two of the at least two color channels are available, a characteristic deviation (in orientation and/or length) from these reference values may be highly indicative of particular health symptoms, syndromes and/or, more generally, disease patterns.

As used herein, electromagnetic radiation particularly relates to visible radiation from which visible image information can be obtained. In other words, imaging systems configured for capturing (visible) image data are primarily addressed. As mentioned above, visible radiation refers to radiation portions which may be sensed by the human eye. However, in some embodiments also wavelength portions adjacent to the visible radiation band may be utilized and detected by a respective sensing device or capturing device. For instance, also near-infrared radiation, infrared radiation and/or ultraviolet radiation may be utilized. As used herein, the term channel signal strength may basically refer to an intensity and/or an amplitude of detected radiation in a respective wavelength portion assigned to a respective (color) channel. The data stream may comprise information involving blood flow related color variations at the subject's skin and/or the subject's tissue where blood flow occurs. As indicated above, primarily a pulsating (AC) portion of the detected image information attributable to the blood flow may be of interest. As used herein, "remote detection" and/or "remotely detected" may refer to a monitoring approach or a monitoring arrangement in which a sensing device, such as a camera or a video camera, is arranged at a considerable distance of the to-be-monitored subject. For example, the distance between the subject and the sensing device may involve at least several centimeters, but may also involve several decimeters or even several meters. Such a remote arrangement allows for fairly unobtrusive measurements. On the other hand, such an arrangement typically also involves huge disturbances and/or distortion due to unstable illumination conditions and/or motion artifacts related to relative motion between the to-be-monitored subject and the sensing device.

The approach presented above is particularly suitable for clinical health monitoring, preferably for neonatal monitoring and/or infant monitoring. Especially neonates and infants suffer from obtrusive contact measurement involving fixedly attached sensors and/or markers. According to the above approach, a subject of interest, such as a neonate, may enjoy a certain degree of freedom while still effective and adequate monitoring is ensured.

The data comparison unit may be configured for performing a "polar" comparison (result: greater-than/less-than) of actual values and reference values, determining of a proportion between actual values and reference values, and/or determining an absolute or relative difference between actual values and reference values. Actual values may be represented by detected channel signal strengths. Reference values may be represented, for instance, by predefined and/or pre-detected channel signal strengths.

According to another aspect, the at least two color channels are associated with a color model, the color model being based on a color model convention allocating respective wavelength portions to the at least two color channels. Basically, a color model may provide sufficient information allowing for digitization of originally analogous image information. In other words, under consideration of the color model, real colors may be transferred into "bits and bites".

According to yet another aspect, the color model is color space based on a color space mapping convention, wherein respective wavelength portions are assigned to respective axes of the color space. Basically the color model may provide a mathematical model describing a digital representation of colors. The color space, however, may be considered as an appropriate color representation based on the respective color model. Such a means may be beneficial since in this way color properties may be presented by geometric entities, such as vectors, which may facilitate handling and processing the respective data.

According to yet another aspect, the color space is an additive color space composed of three color channels. In this way, based on merely three different basic colors a great variety of color nuances may be (re)produced. However, in the alternative, basically also subtractive color spaces may be utilized. For the sake of illustration, but not in a limiting way, the color space may be an RGB color space. A subtractive color space may be a CMY and/or a CMYK color space. In the following, primarily the RGB color model and/or RGB color space is addressed. However, this should not be construed as a limitation. A person skilled in the art may be aware of several alternative and/or substitute color models or color spaces. Furthermore, different color models and different color spaces may be transferred into each other.

According to still another aspect the data comparison unit is further configured for determining a ratio of the detected channel signal strengths of at least two of the at least two color channels and for comparing the ratio of the channel signal strengths with a reference ratio. By way of example, given the exemplary RGB-color space embodiment, a blue to red ratio (B/R) or a red to green and blue ratio (R/(G+B)) may be indicative of respective health symptoms. Comparing such a ratio with a respective reference ratio may reveal significant deviations. In case a deviation-representative value exceeds a predefined threshold, a clear indication of an occurrence of a symptom may be provided.

According to yet another aspect, the system further comprises a symptom analyzer for deriving blood composition-indicative information from a comparison of actual relative channel signal strengths with the reference values. This embodiment makes use of the fact that many diseases and/or health distortions in general may affect the subject's blood composition. Changes in the blood composition of the subject may be detected by comparing actual color information with respective reference color information attributed to a healthy subject.

This embodiment is further developed in that the symptom analyzer is configured for detecting a level of serum bilirubin in the subject's circulating blood under consideration of detected channel strength fluctuations. An increased level of serum bilirubin may be considered as a strong indicator for jaundice. Neonatal jaundice is a yellowing of the skin and other tissues of a new born infant. Jaundice may also occur among adults. The color change is attributed to an increased level of bilirubin. Management and treatment of jaundiced subjects typically requires assessing and monitoring the level of serum bilirubin. According to the above aspect, the system may provide for a long-term unobtrusive bilirubin measurement. In this way, blood sampling and further obtrusive measurement methods can be avoided, at least to a great extend.

According to yet another aspect, the symptom analyzer is configured for detecting a level of bilirubin accumulated in the subject's dermis under consideration of detected constant or quasi-constant channel signal strengths, preferably the symptom analyzer is further configured for deriving an estimate of a serum bilirubin level compared to a skin-bilirubin level. This embodiment makes use of the fact that accumulated bilirubin in the subject's dermis basically alters the DC component of the PPG signal.

In a jaundiced subject, an increased bilirubin level may be present in the subject's circulating blood. However, due to diffusion, bilirubin may also accumulate in the subject's skin tissue. Both bilirubin concentrations in the blood and in the skin may affect the image data from which the desired health information may be obtained. It may be thus beneficial to determine and assess an increase of the bilirubin level in the blood and an increase of the bilirubin level in the skin tissue of the subject. It has been further observed that during treatment of jaundice the level of bilirubin in the skin tissue may be reduced faster than the level of bilirubin in the blood. Consequently, the ability of detecting the level of bilirubin in the blood and the level of bilirubin in the skin tissue allows for the determination of further health-indicative values which may be utilized, for instance, for managing and controlling the treatment of jaundice.

According to still another aspect, the symptom analyzer is configured for detecting relative channels signal strength information indicative of impending suffocation. Especially for neonates and infants, suffocation is a great danger which may lead to severe permanent injuries and even to death. An indication of impending suffocation may be a ratio of hemoglobin or deoxygenated hemoglobin (HB) to oxygenated hemoglobin (HBO2) (HB/HBO2). When suffocation is likely to happen, the HB/HBO2 ratio is increased. This may result in a slight color change which may be characterized by greater amplitudes in the R-channel compared to the G-channel and the B-channel in an RGB color space. Therefore, a characteristic orientation change may be detected and utilized for initiating a suffocation alarm. Given that reference values are obtained beforehand, suitable threshold values may be predefined.

In this connection it is further preferred if the symptom analyzer is configured for assessing oxygenation information under consideration of a ratio of the detected channel signal strengths, the oxygenation information being indicative of a ratio of hemoglobin and oxyhemoglobin in the subject's blood, and for outputting an alert signal when the ratio exceeds a reference threshold.

According to a preferred embodiment, the system further comprises an image sensor for remotely recording image data, the image sensor comprising a responsivity (or: sensitivity) adapted to capture electromagnetic radiation in at least two wavelength portions corresponding to the at least two color channels. In this way, consistent image data encoding and processing may be ensured. When the system also incorporates the image sensor, such as an RGB-camera, a high level of signal integration may be achieved. As indicated above, rather conventional consumer level video cameras may be utilized. It is even further preferred that the camera, the image processor and further components of the system basically apply the same color model. The sensitivity of the image sensor may cover, at least, a considerable portion of visible radiation. However, in some embodiments, the sensitivity of the image sensor may further cover at least a portion of infrared radiation and/or ultraviolet radiation.

According to yet another aspect, the system further comprises a pattern detector for detecting at least one indicative skin portion of the at least one subject of interest.

According to still another embodiment, the system further comprises a treating radiation source for emitting radiation in a particular wavelength range, wherein the treating radiation source is arranged in such a way that the emitted radiation is directed to the subject of interest, preferably the system further comprises a treatment controller for operating the treatment radiation source under consideration of medical condition-indicative data generated by the data comparison unit.

In other words, the system may also comprise a phototherapy function. Phototherapy may be used for treating jaundice. Particularly, the treating radiation source may be embodied as a light source capable of emitting light in the wavelength range of about 400 nm to 500 nm. In this way, increased levels of bilirubin in the subject of interest can be lowered. As indicated above, it is particularly beneficial in this connection that the symptom analyzer may be configured for detecting a level of serum bilirubin in the subject's blood and a level of bilirubin accumulated in the subject's skin tissue. This information, preferably a ratio of a serum bilirubin level to a skin-bilirubin level may be utilized in managing and controlling phototherapy treatment.

In yet another aspect of the present disclosure, a method for extracting physiological information indicative of at least one health symptom from remotely detected electromagnetic radiation is presented, the method comprising the steps of:

receiving a data stream comprising image data representing an observed region comprising at least one subject of interest, wherein the image data comprises wavelength-dependent image information, wherein the wavelength-dependent image information is composed of at least two color channels representative of respective wavelength portions;

detecting channel signals strength information for at least two of the at least two color channels;

comparing detected channel signal strengths with respective reference values.

In yet another aspect of the present disclosure, there is provided a computer readable non-transitory medium having instructions stored thereon which, when carried out on a computer, causes the computer to perform the steps of a method in accordance with the present disclosure.

The program code (or: logic) can be encoded in one or more non-transitory, tangible media for execution by a computing machine, such as a computer. In some exemplary embodiments, the program code may be downloaded over a network to a persistent memory unit or storage from another device or data processing system through computer readable signal media for use within the system. For instance, program code stored in a computer readable memory unit or storage medium in a server data processing system may be downloaded over a network from the server to the system. The data processing device providing program code may be a server computer, a client computer, or some other device capable of storing and transmitting program code.

As used herein, the term "computer" may stand for a large variety of processing devices. In other words, also mobile devices having a considerable computing capacity can be referred to as computing devices, even though they provide less processing power resources than standard "computers". Needless to say, such a "computer" can be part of a medical device and/or system. Furthermore, the term "computer" may also refer to a distributed computing device which may involve or make use of computing capacity provided in a cloud environment. The term "computer" may also relate to medical technology devices, fitness equipment devices, and monitoring devices in general, that are capable of processing data.

Preferred embodiments of the disclosure are defined in the dependent claims. It should be understood that the claimed method and the claimed computer program can have similar preferred embodiments as the claimed system and as defined in the dependent system claims.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
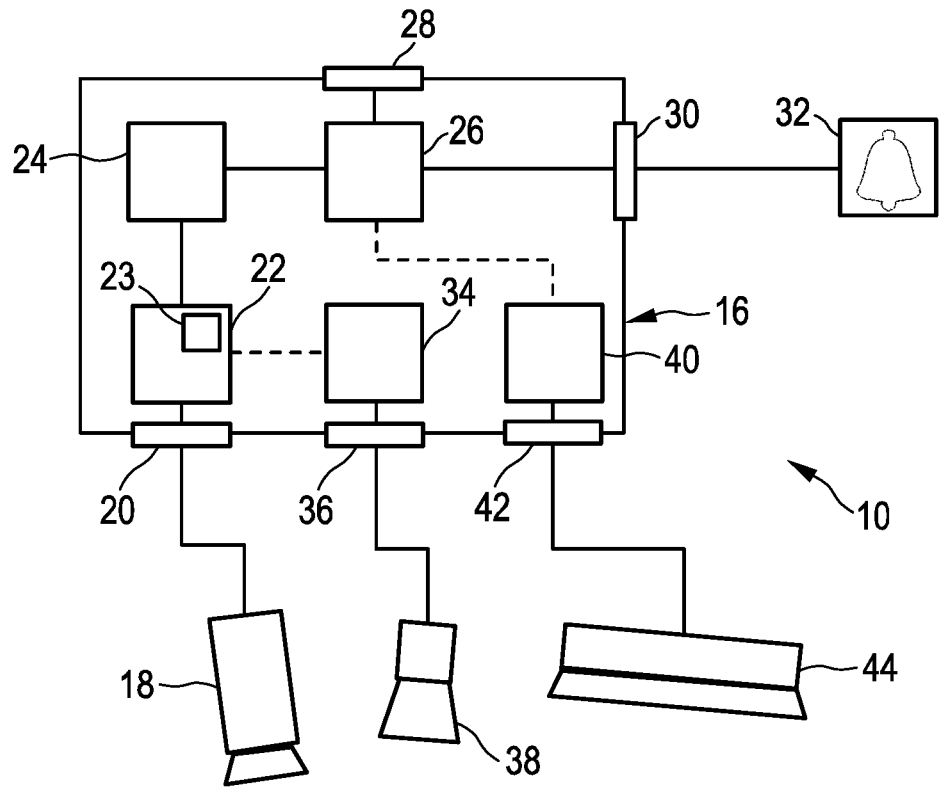
FIG. 1 shows a simplified schematic illustration of a system according to an embodiment of the present disclosure.
Figure 1:
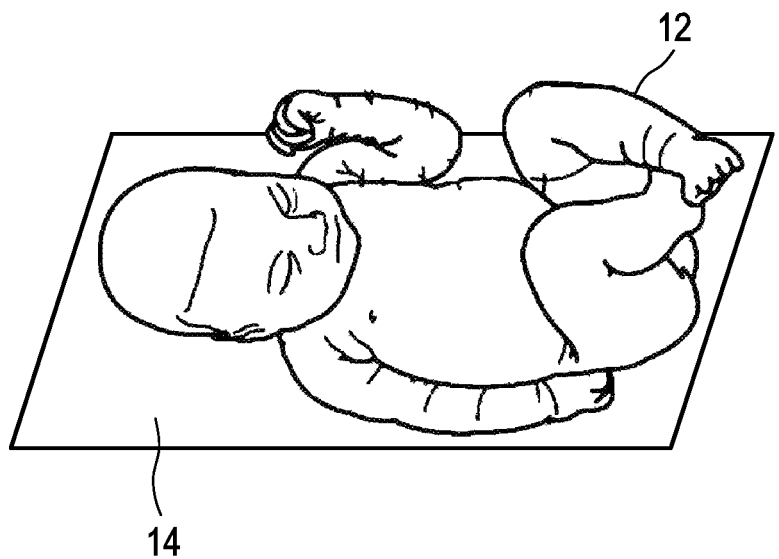

FIG. 1 shows a schematic illustration of a set-up of a system 10 in accordance with an embodiment of the present disclosure. By way of example, but not to be understood in a limiting way, the system 10 may be used in neonatal care units for monitoring a subject 12 such as a neonate or infant. In general, the system 10 may be configured for monitoring subjects 12 such as patients or, more generally, human beings or living beings. Especially neonates may be positioned on a lying surface 14 which may be part of a hospital bed or an arrangement specifically adapted for receiving and supporting newborn infants, such as an incubator.

Neonatal jaundice (also known as hyperbilirubinemia) often occurs among newborns since the neonate's liver might be underdeveloped at the very beginning and therefore not able to excrete and, consequently, reduce the level of bilirubin. So-called unconjugated bilirubin may be formed as a degradation by-product during the destruction of old red blood cells. Since the neonate's organism may not be capable of efficiently absorb and reduce bilirubin, unconjugated bilirubin levels often raise in newborns. When a level of unconjugated bilirubin rises beyond a given binding capacity, unconjugated bilirubin may diffuse out of the circulatory system and enter neighboring tissues. Typically, the diffusion of free bilirubin into the subject's 12 skin tissue may cause a characteristic yellowing of the skin tone. Especially for premature neonates, increased bilirubin levels may even lead to severe brain dysfunction, for instance to kernicterus. Since the liver function and the circulatory system in general is less developed among premature neonates they face a higher risk of severely suffering from increased bilirubin levels.

Since conventional approaches for measuring and monitoring the bilirubin levels in the subject 12 often have been experienced as being unpleasant and obtrusive, some embodiments of the present disclosure seek for providing reliable and unobtrusive monitoring techniques which may even enable long-term monitoring. To this end, the system 10 may comprise a data processing device 16 which may be coupled with or incorporate a sensor or camera 18. Since the system 10 is configured for processing image data, such as video data, the sensor 18 may be embodied by a rather conventional video camera, for instance. Fairly unobtrusive measurement may be achieved since the camera 18 may be arranged at a distance from the subject 12 to be monitored. In other words, according to preferred embodiments of the present disclosure, the sensor 18 does not have to be embodied by contact sensors to be attached to the subject's skin. For instance, the sensor 18 may incorporate a CCD-array or a CMOS-array for sensing and digitizing image information, such as visible radiation and, in some embodiments, infrared radiation and/or ultraviolet radiation. In this context, the term visible radiation may also refer to radiation portions that are primarily "visible" to the sensor 18. The camera 18 may be connected with an image processor 22 via an interface 20. Via the interface 20, image data may be transmitted to the image processor 22. Preferably, the camera 18 is configured for decomposing and transferring analogous image information into digital image information comprising at least two color channels.

For instance, the camera 18 may be arranged as a video camera capable of capturing and generating RGB-image data. Image data, such as RGB-image data may be processed accordingly by the image processor 22. For instance, the image processor 22 can be configured for detecting (relative) channel signals strength information for at least some, preferably for all of the color channels the image data is composed of. As indicated above, characteristic channel signal strengths or channel signal strength ratios may be highly indicative of physical conditions or, more specifically, health conditions, of the subject 12. The data processing device 16 may further comprise a pattern detector 23 for detecting at least one indicative skin portion of the at least one subject of interest 12. As known in the art, the pattern detector 23 may utilize skin detection algorithms so as to distinguish between (indicative) skin portions and (non-indicative) surrounding portions which also may be present in the image data.

The image processor 22 is basically configured for condensing the digital image information into dimension-reduced (relative) strength information. To this end, the image processor 22 may be capable of transferring a plurality of image entities (or: pixels) into a single entity representing a respective pattern, wherein the single entity is composed of basically two or more values indicating respective color channel signal strengths. In other words, the desired information contained in a two-dimensional (colored) pixel pattern may be agglomerated and transferred into a single index element or color vector characterized by a length and an orientation. The length and the orientation of the color vector are attributable to respective signal strengths at least some of the color channels.

Preferably, the image processor 22 is further configured for providing for image data normalization. For instance, time-based normalization can be applied to captured image data. Given the exemplary embodiment implementing R (red), G (green) and B (blue) channels, the image processor 22 may be configured for dividing their actual values by a respective time-average value. The time-average value for each of the channels may be based on a running average over a window having a predefined size. Alternatively, the time-average value may be based on an average over a time-interval, wherein all samples (each actual value) in a specified time-interval may be divided by the same average over that interval. In this way, a variation in the strength and/or color of any illumination device illuminating the subject 12 may be sufficiently attenuated so as to avoid and/or reduce disturbing influences.

A data stream comprising the channel signal strength information detected by the image processor 22 may be delivered to a data comparison unit 24 for comparing the detected channel signal strengths with respective reference values. In other words, the data comparison unit 24 may be configured for assessing characteristic differences of the channel signal strengths with respect to reference values (e.g., in terms of length and/or orientation). As indicated above, characteristic deviations in length and/or in orientation may be highly indicative of particular health symptoms. For comparing the data and/or for assessing differences, the data comparison unit 24 may be provided with reference data from which the reference values may be obtained. Reference data may be generated, for instance, upon monitoring healthy subjects 12.

Based on characteristic deviations, the presence of characteristic symptoms may be assessed. However, the data processing device 16 may further comprise, in the alternative or in addition, a symptom analyzer 26 for deriving blood composition-indicative information from a comparison of actual (relative) signal strengths with the reference values. So the symptom analyzer 26 can make use of the fact that many characteristic symptoms may involve variances or changes of the blood composition of the subject 12 which may find expression in slight color changes and/or deviations of the AC portion of the PPG signal which may be detected by the system 10. As indicated above, slight color changes occurring in the patient's blood and/or skin tissue may be attributed, for instance, to an increased level of bilirubin and/or may be a strong indicator for an impending suffocation incident. At least one of the data comparison unit 24 and the symptom analyzer 26 may be further configured to provide output data which may be used for further analyses and/or for display measures.

The output data may be provided at the output interface 28. Furthermore, at least one of the data comparison unit 24 or the symptom analyzer 26 can be adapted for generating an alert signal which may be submitted to a respective alert signal interface 30 which may be coupled with an alert unit 32. Especially when severe symptoms are detected, the alert unit 32 may be triggered so as to generate an alert signal for alarming the subject 12, medical staff or, more generally, care taking persons about severe deviations detected by the system 10. Consequently, counter measures may be taken accordingly.

The data processing device 16 may be further coupled with a monitoring radiation source 38. The monitoring radiation source 38 may be embodied by a light source arranged for illuminating a portion of the to-be-monitored subject 12 which is observed by the camera 18. Consequently, relatively stable illumination conditions may be achieved contributing to noise reduction and/or disturbance minimization. The monitoring radiation source 38 may be embodied by a conventional light source emitting light in a particular wide wavelength range, preferably adapted to the sensitivity of the camera 18. Also the monitoring radiation source 38 may be controlled and/or managed by the data processing device 16. To this end, the monitoring radiation source 38 may be connected via an interface 36 to a monitoring light controller 34. The monitoring light controller 34 may be coupled with at least one of the image processor 22, the data comparison unit 24 and the symptom analyzer 26. In doing so, the data processing device 16 may be provided with illumination information facilitating (image) data processing.

According to some exemplary embodiments, the data processing device 16 may be further coupled with a treating radiation source 44. This applies in particular when the system 10 is further configured for providing phototherapy. Phototherapy may be a suitable treatment for increased bilirubin concentrations in the subject 12, especially for neonates. Phototherapy treatment may typically involve at least one light source 44 capable of emitting light in the wavelength range of about 400 to about 500 nm. The light directed at the subject's 12 skin may interact with the accumulated bilirubin in the subject's 12 skin tissue. In this way, the bilirubin level may be sufficiently decreased over time. Preferably, also the treating radiation source 44 is connected to the data processing device 16. For instance, the treating radiation source 44 may be connected via an interface 42 with a treatment controller 40. The treatment controller 40 may be connected to at least one of the image processor 22, the data comparison unit 24 or the symptom analyzer 26. Provided that an increased level of bilirubin is detected by the data processing device 16, the treating radiation source 44 may be controlled so as to selectively emit radiation to the to-be-treated subject 12. On the other hand, being aware of actual phototherapy treatment, the data processing device 16 may consider this information when processing the respective data. As indicated above, phototherapy may efficiently decrease the level of bilirubin in the skin tissue of the subject 12. However, typically the serum bilirubin level in the subject's blood may not be reduced accordingly at the same time. Having knowledge of phototherapy treatment taking place allows for assessing a serum bilirubin concentration more precisely.

The image processor 22, the data comparison unit 24 (and, if provided, any of the symptom analyzer 26, the monitoring light controller 34 and the treatment controller 40) may be implemented by a common processing unit, such as the data processing device 16, which can be considered as a computing device, or at least, part of a computing device driven by respective logic commands (program code) so as to provide for desired data processing. The data processing device 16 may further comprise several components or units which may be addressed in the following. It should be understood that each component or unit of the data processing device 16 may comprise a number of processors, such as multi-core processors or single-core processors. At least one processor can be utilized by the data processing device 16. Each of the processors can be configured as a standard processor (e.g. central processing unit) or as a special purpose processor (e.g. graphics processor). Hence, the data processing device 16 can be suitably operated so as to distribute several tasks of data processing to adequate processors.

The data processing device 16 as well as at least one of the interfaces 20, 28, 30, 36, 42 can be embodied in a common processing apparatus or housing. Basically, the imaging unit or camera 18 and the monitoring radiation source 38 (and, if any, the treating radiation source 44) are generally external elements, but may also be integrated into a common housing with the data processing device 16. Furthermore, each of the image processor 22, the data comparison unit 24, and the symptom analyzer 26, the monitoring light controller 34 and the treatment controller 40 may be implemented by hardware means or by software means. Also a hybrid implementation including hardware and software components may be envisaged.

Figure 2:
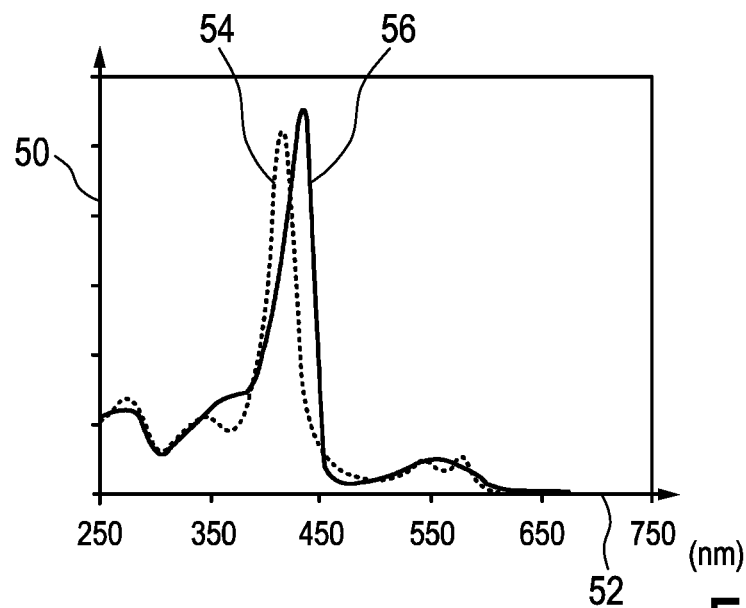
FIG. 2 shows exemplary absorption spectrum charts for hemoglobin and for oxygenated hemoglobin.
Figure 3:
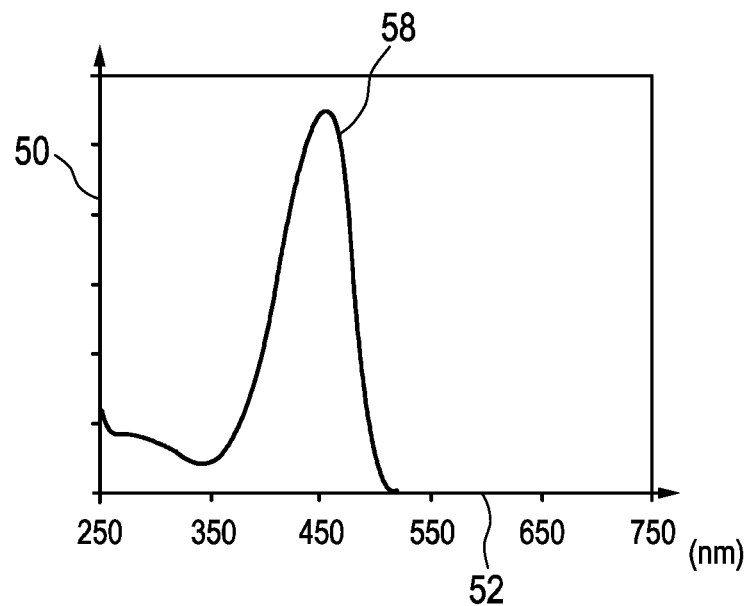
FIG. 3 shows an exemplary absorption spectrum chart for bilirubin.

FIG. 2 and FIG. 3 illustrate exemplary absorption spectra diagrams for blood (including hemoglobin and oxygenated hemoglobin) and for bilirubin. In each of the diagrams, an axis of abscissas indicated by reference number 52 represents a respective wavelength interval covering a range between about 250 nm and 750 nm. An ordinate axis 50 represents a (qualitative) absorption behavior of the respective materials. In FIG. 2, a graph representing the absorption spectrum for oxygenated hemoglobin (HBO2) is indicated by reference number 54. A graph representing the absorption spectrum of (deoxygenated) hemoglobin (HB) is indicated by reference number 56. As can be clearly seen, enrichment of hemoglobin with oxygen slightly shifts a respective absorption peak. Based on this phenomenon, for instance, impending suffocation may be detected since accordingly basically a level of (deoxygenated) hemoglobin rises while a level of oxygenated hemoglobin decreases. This may result in slight color variations, compared with a healthy subject. Assuming that the system 10 is configured for operating on the basis of an RGB color space, the above variation may result in greater pulsatility in the R-channel when compared to the G- and B-channels. Therefore, a corresponding slight orientation change of a color vector in the RGB color space may be detected.

FIG. 3 illustrates an absorption spectrum of bilirubin wherein a respective graph is indicated by reference number 58. When the level of bilirubin in the monitored subject 12 is increased, the characteristic bilirubin absorption pattern may influence detected channel signal strengths accordingly. For instance, a respective RGB signal may be shifted to an increased pulsation amplitude in the B-color channel and to a moderately increased pulsation amplitude in the G-channels while the pulsation amplitude in the R-channel may be decreased. Also this variation may result in a characteristic orientation change of the color vector in the color space.

In other words, according to the above aspects, the present disclosure may aim at a "mediate" qualitative detection of abnormal health conditions. Provided that reference data characterizing healthy subjects can be obtained beforehand, potentially dangerous health conditions such as jaundice and/or starting suffocation may be reliably detected during long term monitoring.

Figure 4:
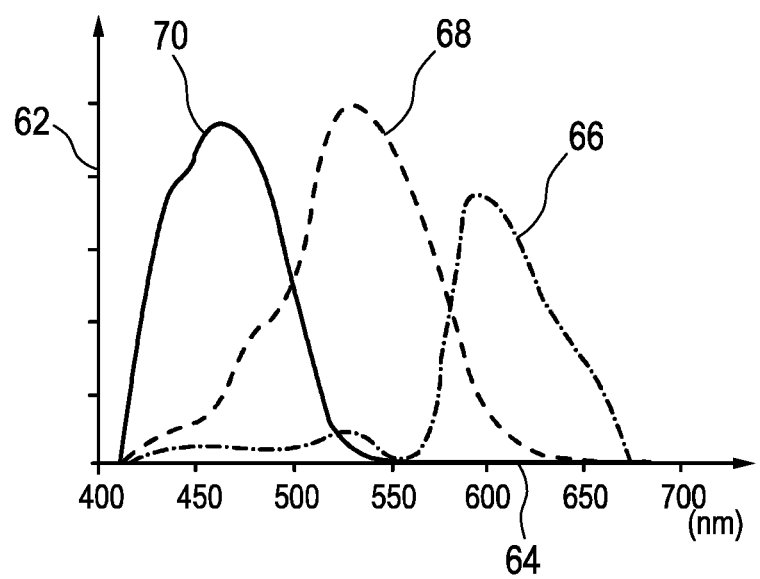
FIG. 4 shows an exemplary diagram indicating spectral sensitivity characteristics of a three-channel camera.

FIG. 4 illustrates a diagram indicating a spectral responsivity characteristic of an exemplary sensor or camera 18. An axis of abscissas 64 may stand for a particular wavelength while an ordinate axis 62 represents a corresponding sensitivity. A graph 66 represents an R-channel. A graph 68 represents a G-channel. A graph 70 represents a B-channel. In total, the graphs 66, 68, 70 may cover a visible light spectral portion visible to the human eye. Given that for each of the channels R, G, B respective input signals are separately captured and stored by the camera 18 respective corresponding data values or entities allow for a color representation in the RGB color space. Consequently, multi-channel color information may be represented by a color vector in a respective multi-dimensional color space.

Figure 5:
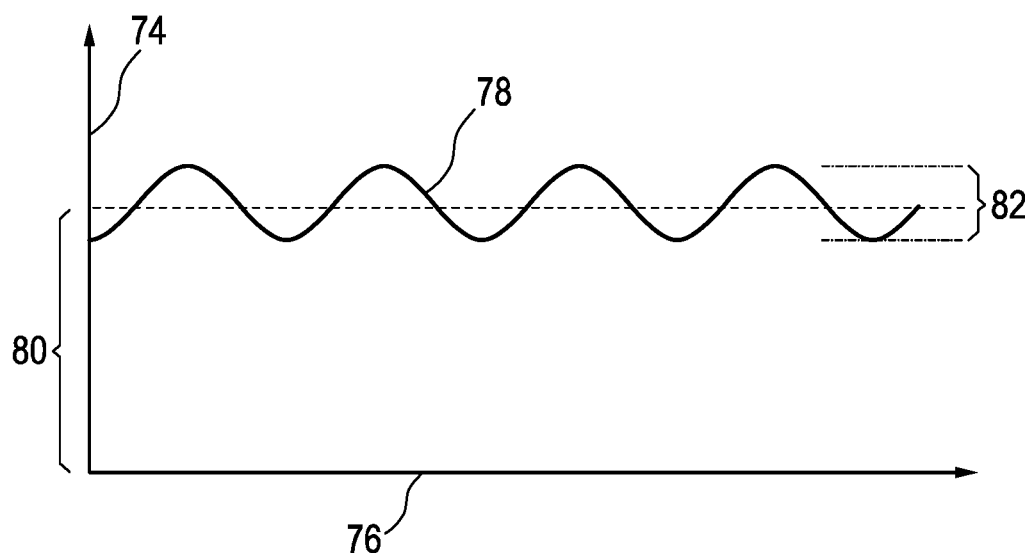
FIG. 5 illustrates a schematic illustration of a pulsating PPG signal composed of a considerably constant (DC) portion and an overlapping alternating pulsatile (AC) portion.

FIG. 5 illustrates a representation of an exemplary PPG signal indicated by reference numeral 78 over time. An axis of abscissas 76 represents time. An ordinate axis 74 basically represents a signal strength. Typically, the PPG signal 78 is composed of a relatively large constant portion or DC portion, refer to reference number 80. Furthermore, the PPG signal 78 is characterized by a relatively small pulsating or alternating portion 82. The pulsations in the alternating portion or AC portion 82 may be attributed to blood pulsation in the subject 12. However, further information can be obtained from the AC portion 82. The overall PPG signal 78 illustrated in FIG. 5 may be composed of a plurality of color channels. Consequently, the representation provided in FIG. 5 may involve a dimensional reduction, for the sake of illustration. In other words, each value or entity of the PPG graph 78 may be composed of two or more components, for instance of respective R-values, G-values and B-values.

Figure 6:
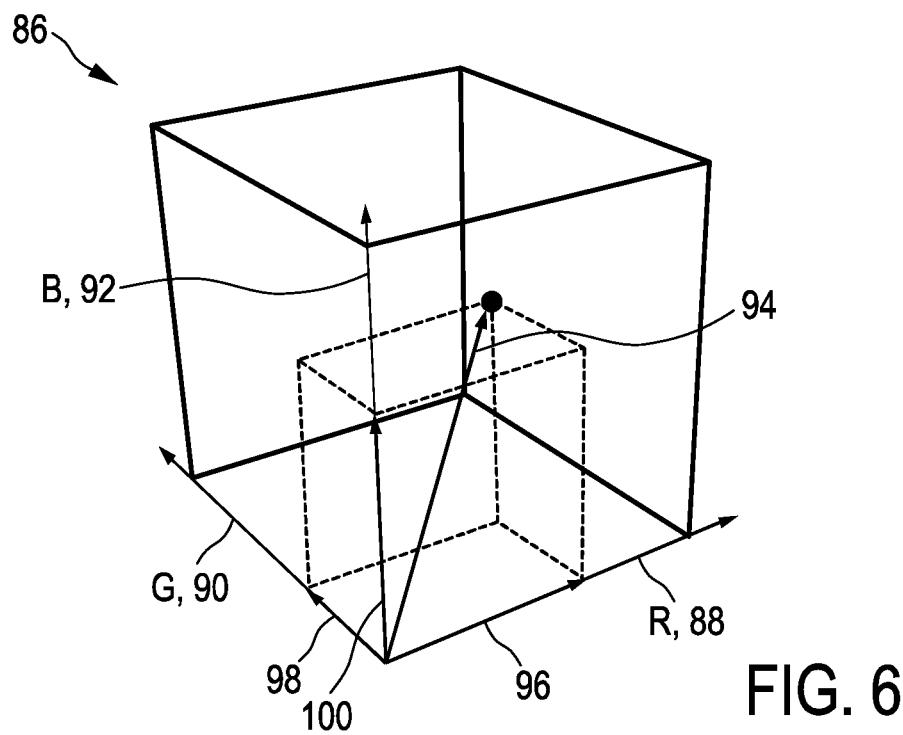
FIG. 6 illustrates a schematic representation of an exemplary (three-dimensional) color space in which a color vector is present.
Figure 7:
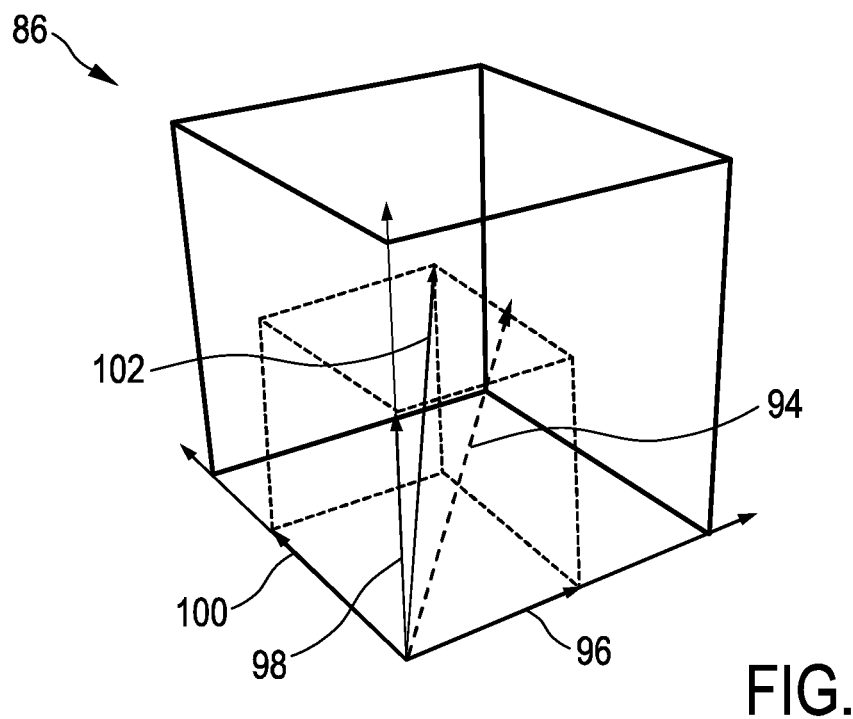
FIG. 7 illustrates another representation of the color space according to FIG. 6, wherein another color vector is present having a different orientation and length.

FIG. 6 and FIG. 7 illustrate a three-dimensional representation of a multi-channel color space 86. Each of the color spaces 86 may represent absolute PPG signals (including the DC and the AC portion) or relative PPG signals (including the AC portion). For the sake of simplicity, the color space 86 may be referred to as an RGB-color space composed of an R-channel (reference number 88), a G-channel (reference number 90), and a B-channel (reference number 92). FIG. 6 further illustrates an index element or color vector 94. The color vector 94 may be a three-dimensional vector having three respective components. For instance, the color vector 94 may be composed of component vectors 96, 98, 100 assigned to respective axis or channels 88, 90, 92. A pulsation or alternating variation of the PPG signal 78 (reference number 82 in FIG. 5) may involve a corresponding alternating characteristic variation (in terms of orientation and length) of the color vector 94 over time. In this connection, FIG. 7 illustrates another color vector 102. For the sake of simplicity, the color vectors 94 and 102 may represent opposite extreme values (minima and maxima) of the alternating pulsating portion 82 of the PPG signal 78 in FIG. 5. Over time, due to blood pulsation an actual color vector may be alternatingly moved along a path between the "boundary color" color vectors 94 and 104.

Figure 8:
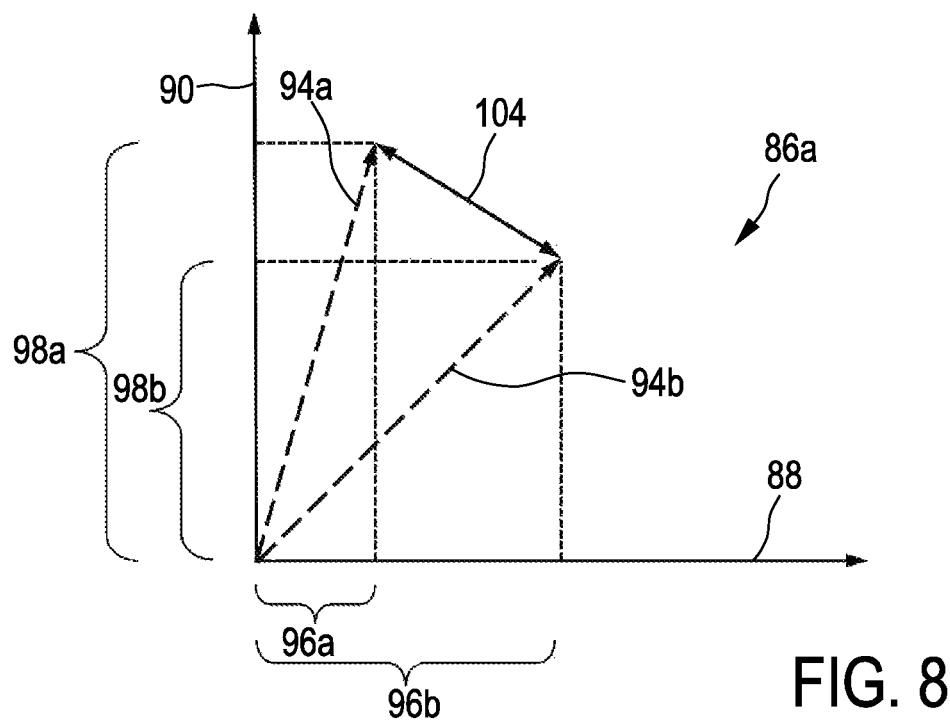
FIG. 8 exemplifies a (two-dimensional) color space in which two color vectors are presented, wherein also an exemplary path or curve of an alternating motion of the pulsating color vector is indicated.
Figure 9:
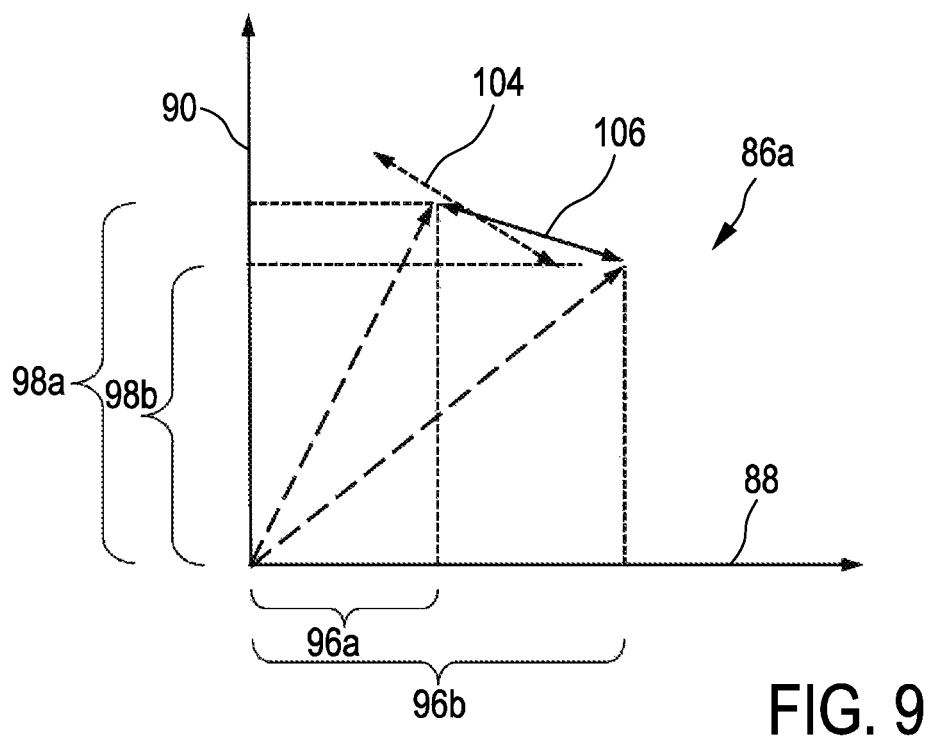
FIG. 9 illustrates a color space in accordance with FIG. 8, wherein another path or curve of the alternating motion of the pulsating color vector is illustrated having a different length and orientation when compared with the path or curve illustrated in FIG. 8.

Such a relative color variation is indicated by reference number 104 in FIG. 8. FIG. 8 and FIG. 9 represent simplified two-dimensional color spaces 86a. Particularly for illustration purposes, the color spaces 86a are merely composed of two color channels 88, 90. In FIG. 8 two color vectors 94a, 94b are present which may represent extreme values of the pulsating PPG signal component. Reference number 104 indicates a resulting relative color path or curve. The relative color path 104 typically may have a curved shape. However, for the sake of simplicity, the relative color path 104 in FIG. 8 basically comprises a straight line. For instance, the relative color path 104 may represent a reference color path of blood flow induced pulsations for a healthy subject 12. The color path 104 may be characterized by a given orientation and length. The relative color path 104 may also be described by respective pairs of values 98a, 96a and 98b, 96b indicating respective signals strength at the first color channel 88 and the second color channel 90.

The relative color path 104 representing a healthy subject is indicated in FIG. 9 by a dashed double arrow. Furthermore, a deviating relative color path or curve 106 is presented in FIG. 9. The relative color path 106 may represent a subject 12 suffering from jaundice or impending suffocation. Further symptoms may be detected upon monitoring and investigating characteristic deviations in a present relative color path in a monitored subject 12. Needless to say, the desired deviation to be detected may also be obtained through monitoring the color vectors 94a, 94b as such. A comparison of signal strengths or relative signal strengths for at least some of the at least two color channels 88, 90 may also result in highly indicative values.

Figure 10:
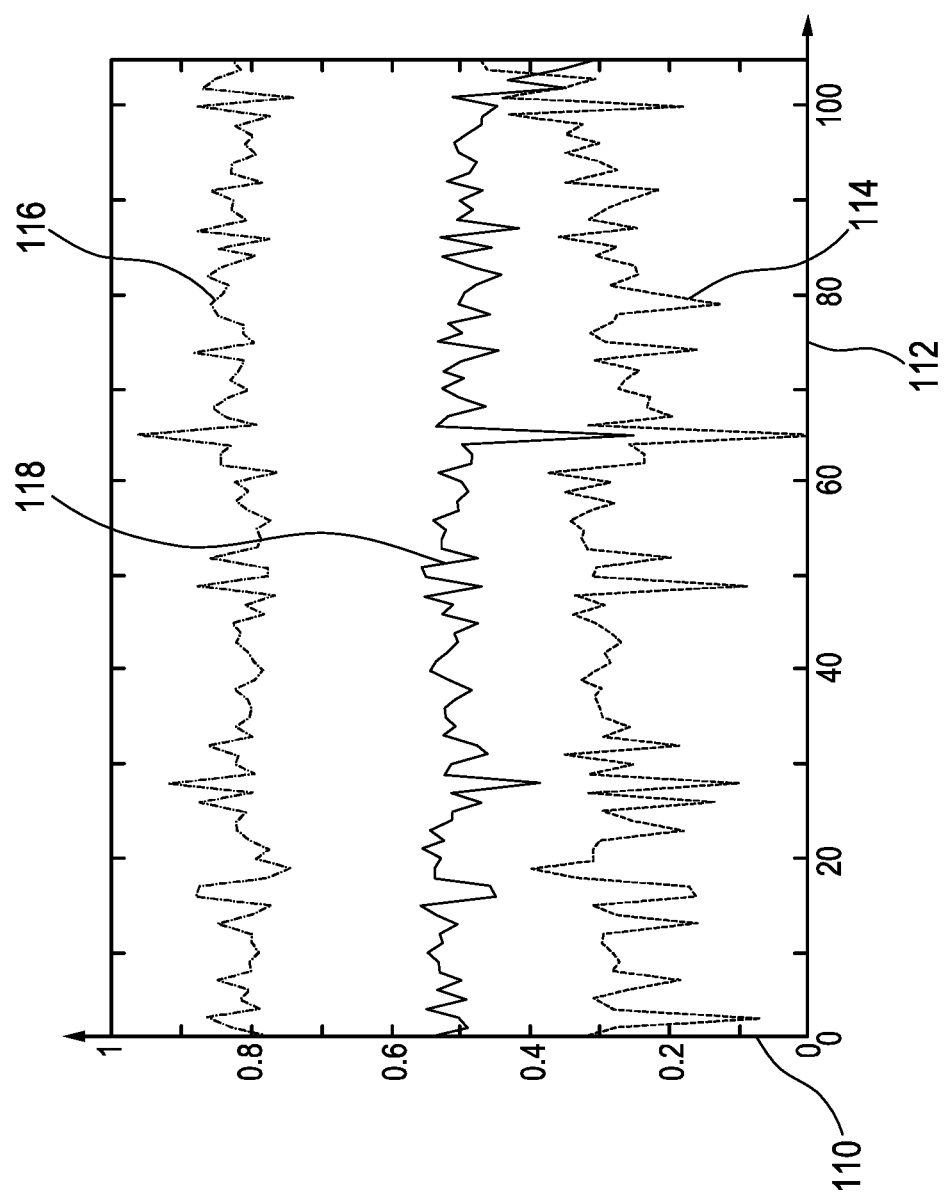
FIG. 10 illustrates relative blood pulsation-related amplitudes for a set of reference subjects in three respective wavelength portions or color channels.

FIG. 10 shows an illustrative diagram indicating components of a blood pulsation-indicative PPG signals for a data set over 105 exemplary (healthy) subjects with different skin types. On an axis of abscissas 112 the respective number of the individuals is denoted, wherein the skin tone of the subjects ranges from very light on the left side to very dark on the right side. An ordinate axis 110 indicates a qualitative relative signal strength in the respective channels R, G, B. Reference number 115 indicates a red color channel (R), reference number 118 indicates a blue color channel (B) and reference number 116 indicates a green color channel (G). Despite several outliers, the detected signal also referred as blood volume pulse (or: Pbv) is remarkably stable.

The main chromophores (or: colorants) for light with a wavelength between 400 and 950 nm in healthy human skin are melanin and blood. The blood is contained in the vascular system and only the arterial part exhibits the pulsation leading to the color variation over time. The melanin is concentrated in the epidermis which consequently acts as a filter between the dermis, including blood vessels, and any camera and light source. Since the blood volume pulse may be measured in a normalized color space (e.g., actual values divided by time-average values), the effect of the filtering may be removed in the normalized data and, consequently, the skin-type has no major influence on the orientation of the blood volume pulse or the respective color vector.

It is therefore concluded that a corresponding orientation of the PPG signal vector (see the color vectors 94, 102 in FIGS. 6 through 9) may be utilized as a considerably robust health indicator for symptoms of several diseases and/or health conditions which may affect at least one of the skin color (or: skin-tissue color) or the color of the pulsating blood. Typically, both the skin color and the blood color may be affected. Again referring to FIG. 10, it is concluded that for subjects having dark skin a relative signal strength in the blue channel may be decreased while the relative signal strength in the red channel may be increased. This effect may be attributed to specular reflection which is likely to occur among subjects having dark skin. However, this influence may be observed and compensated accordingly. For further improving monitoring accuracy respective reference values may be chosen so as to reflect the subject's 12 preconditions on a personal level. This may even involve providing further contextual information describing the to-be-monitored subject 12. Contextual information may relate to the observed skin color tone and, if any, the duration and/or intensity of phototherapy, for instance. Furthermore, known health issues the subject 12 is facing may be provided beforehand so as to further improve the response accuracy or detection accuracy of the system.

Figure 11:
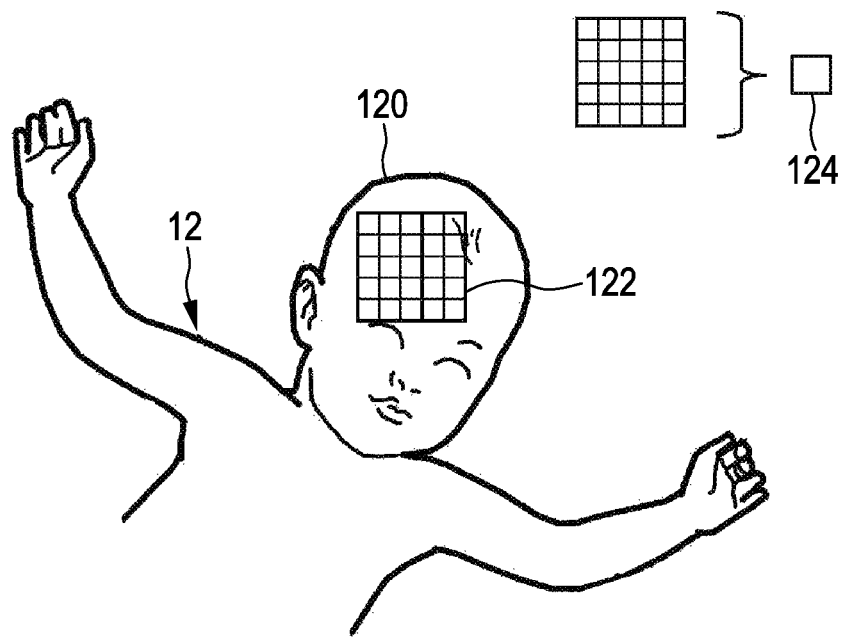
FIG. 11 illustrates a to-be monitored subject, wherein an indicative skin portion is highlighted from which a mean PPG general may be obtained.

Referring to FIG. 11, another exemplary illustration of a to-be-monitored subject 12 is provided. When monitoring the subject 12, the sensor or video camera 18 (FIG. 1) may be controlled and/or adjusted so as to basically monitor an indicative skin portion 120 of the subject 12. The system 10, particularly the data processing device 16, may be further configured for applying pixel pattern-based motion compensation or, more generally, spatial signal normalization to the detected and captured video data. An area of interest of the subject 12 in FIG. 11 is masked with an exemplary pixel pattern 122. The pixel pattern 122 may cover both basically indicative portions of the subject 12 and basically non-indicative portions. When agglomerating respective signal pixel values of the pixel pattern 122, a mean pixel value can be derived which is denoted by reference number 124 in FIG. 11. In this way, a multi-dimension video signal may be transferred into a color-representative signal basically composed of a single entity. In this way, undesired motion of the subject 12 can be compensated or, at least, attenuated in the resulting mean color signal 124.

Figure 12:
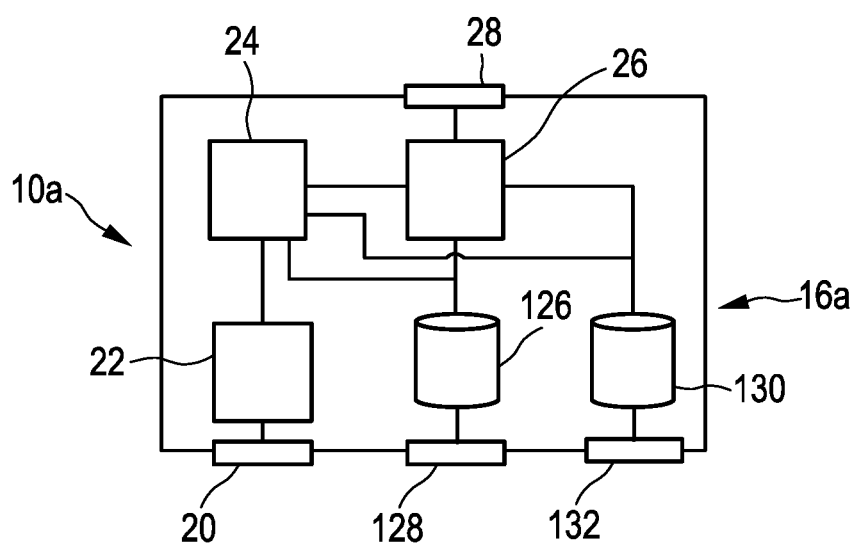
FIG. 12 shows a simplified schematic illustration of a system according to an alternative embodiment of the present disclosure.

FIG. 12 shows an alternative arrangement of a system 10a for extracting physiological information indicative of at least one health symptom from remotely detected electromagnetic radiation. Particularly, an alternative data processing device 16a is schematically illustrated in FIG. 12. As to their basic set-up both the data processing device 16 illustrated in FIG. 1 and the data processing device 16b illustrated in FIG. 12 may be similarly configured. The data processing device 16a may further comprise a memory unit or storage 126 which may also be referred to as reference memory unit or storage. The reference memory unit or storage 126 may be configured for storing reference values representing expected channel signals strength in the color channels the input video data is basically composed of which are attributed to healthy subjects 12. In this way, a set of reference values may be provided based on which occurring deviations (including orientation and/or length changes) may be detected and assessed accordingly. The reference memory unit or storage 126 may be connected to at least one of the data comparison unit 24 or the symptom analyzer 26. The reference memory unit or storage 126 may be further connected to a respective interface 128 where input data may be received.

The data processing device 16a may further comprise a calibration input memory unit or storage 130. The calibration input memory unit or storage 130 may be configured for storing further calibration information intended for use at the personal level of the to-be-monitored subject 12. To this end, for instance, contextual information may be provided via an interface 132. Consequently, the reference memory unit or storage 126 may comprise overall basic reference information while the calibration input memory unit or storage 130 may comprise further personal calibration information. Also the calibration input memory unit or storage 130 may be connected to at least one of the data comparison unit 24 and the symptom analyzer 26. The memories or storages 126, 130 can take the form of (real) hardware memories or (virtual) software memories. Particularly, the memories or storages 126, 130 can be embodied by the same memory element.

Figure 13:
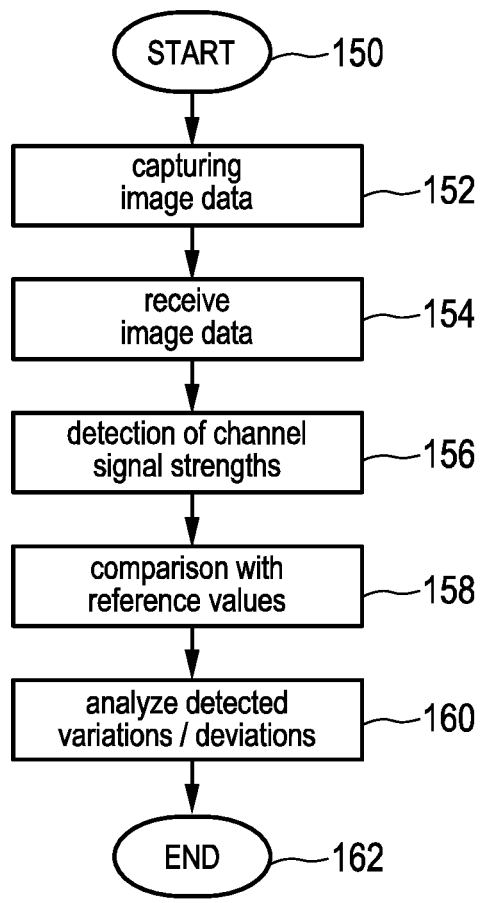
FIG. 13 shows an illustrative block diagram representing several steps of an embodiment of a method in accordance with the present disclosure.

FIG. 13 schematically illustrates a method for extracting physiological information indicative of at least one health symptom from remotely detected electromagnetic radiation. At a first step 150, the method and a related process may be initiated. A step 152 may follow which comprises remotely capturing an image data stream comprising image data representing an observed region comprising at least one to-be-monitored subject of interest. In a further step 154, the image data stream may be received by a data processing device. The image data stream may be basically composed of multi-channel image data, such as three-channel color image data. For instance, RGB-image data may be transferred to the data processing device. In yet another step 156, channel signal strength information may be detected for each of the plurality of color channels. The step 156 may further include the detection of relative channel signal strength information. A further step 158 may follow comprising a comparison of detected channel signal strengths or relative channel signal strengths with respective reference values. Another step 160 may follow which may comprise analyzing detected variations and/or deviations so as to eventually assign or attribute characteristic deviations to corresponding health symptoms. At a further step 162, the method may terminate. Needless to say, the method may be used in a continuous monitoring process, such as a long-term monitoring process. Of course, also short-term or spot check monitoring may be envisaged.

By way of example, the present invention can be applied in the field of health care, e.g. unobtrusive remote patient monitoring, general surveillances, security monitoring and so-called lifestyle environments, such as fitness equipment, or the like. Applications may include monitoring of oxygen saturation (pulse oximetry), heart rate, blood pressure, cardiac output, changes of blood perfusion, assessment of autonomic functions, and detection of peripheral vascular diseases. Needless to say, in an embodiment of the method in accordance with the disclosure, several of the steps described herein can be carried out in changed order, or even concurrently. Further, some of the steps could be skipped as well without departing from the scope of the invention.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable (non-transitory) medium, such as an optical storage medium or a solid-state medium supplied together with or as part of other hardware, but may also be distributed in other forms, such as via the Internet or other wired or wireless telecommunication systems. Furthermore, the different embodiments can take the form of a computer program product accessible from a computer usable or computer readable medium providing program code for use by or in connection with a computer or any device or system that executes instructions. For the purposes of this disclosure, a computer usable or computer readable medium can generally be any tangible apparatus that can contain, store, communicate, propagate, or transport the program for use by or in connection with the instruction execution device.

Furthermore, the different embodiments can take the form of a computer program product accessible from a computer usable or computer readable medium providing program code for use by or in connection with a computer or any device or system that executes instructions. For the purposes of this disclosure, a computer usable or computer readable medium can generally be any tangible device or apparatus that can contain, store, communicate, propagate, or transport the program for use by or in connection with the instruction execution device.

In so far as embodiments of the disclosure have been described as being implemented, at least in part, by software-controlled data processing devices, it will be appreciated that the non-transitory machine-readable medium carrying such software, such as an optical disk, a magnetic disk, semiconductor memory or the like, is also considered to represent an embodiment of the present disclosure.

The computer usable or computer readable medium can be, for example, without limitation, an electronic, magnetic, optical, electromagnetic, infrared, or semiconductor system, or a propagation medium. Non-limiting examples of a computer readable medium include a semiconductor or solid state memory, magnetic tape, a removable computer diskette, a random access memory (RAM), a read-only memory (ROM), a rigid magnetic disk, and an optical disk. Optical disks may include compact disk-read only memory (CD-ROM), compact disk-read/write (CD-R/W), and DVD.

Further, a computer usable or computer readable medium may contain or store a computer readable or usable program code such that when the computer readable or usable program code is executed on a computer, the execution of this computer readable or usable program code causes the computer to transmit another computer readable or usable program code over a communications link. This communications link may use a medium that is, for example, without limitation, physical or wireless.

A data processing system or device suitable for storing and/or executing computer readable or computer usable program code will include one or more processors coupled directly or indirectly to memory elements through a communications fabric, such as a system bus. The memory elements may include local memory employed during actual execution of the program code, bulk storage, and cache memories, which provide temporary storage of at least some computer readable or computer usable program code to reduce the number of times code may be retrieved from bulk storage during execution of the code.

Input/output, or I/O devices, can be coupled to the system either directly or through intervening I/O controllers. These devices may include, for example, without limitation, keyboards, touch screen displays, and pointing devices. Different communications adapters may also be coupled to the system to enable the data processing system to become coupled to other data processing systems, remote printers, or storage devices through intervening private or public networks. Non-limiting examples are modems and network adapters and are just a few of the currently available types of communications adapters.

The description of the different illustrative embodiments has been presented for purposes of illustration and description and is not intended to be exhaustive or limited to the embodiments in the form disclosed. Many modifications and variations will be apparent to those of ordinary skill in the art. Further, different illustrative embodiments may provide different advantages as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated. Other variations to the disclosed embodiments can be understood and effected by those skilled in the art in practicing the claimed invention, from a study of the drawings, the disclosure, and the appended claims.

Any reference signs in the claims should not be construed as limiting the scope.

The invention claimed is:

1. A photoplethysmographic monitoring system configured for extracting physiological information indicative of at least one health symptom from detected electromagnetic radiation, the photoplethysmographic monitoring system comprising:
one or more sensors configured to generate output signals conveying information related to skin radiation of a subject, the skin radiation information including wavelength-dependent image information, wherein the wavelength-dependent image information is composed of at least two color channels representative of respective wavelength portions, and the wavelength-dependent image information comprises a pulsating signal component; and
one or more processors configured by machine-readable instructions to:
receive the skin radiation information;
detect relative channel signal strength information for the at least two color channels, wherein the relative channel signal strength information corresponding to the at least two color channels is represented by color vectors, and the color vectors are moved along a path between minima and maxima corresponding to the pulsating signal component;

compare the color vectors' path with a reference vector path, wherein the reference vector path is obtained by monitoring healthy subjects;

determine blood composition-indicative information of the subject based on the comparison of the color vectors' path and the reference vector path; and determine a level of serum bilirubin in the subject's circulating blood based on signal strength fluctuations.

2. The photoplethysmographic monitoring system of claim 1, wherein the one or more processors are further configured to:
(i) determine a ratio of the at least two color channels,
(ii) compare the determined ratio with a reference ratio, the reference ratio obtained by monitoring the healthy subjects, and
(iii) determine blood composition-indicative information based on the comparison of the determined ratio and the reference ratio.

3. The photoplethysmographic monitoring system of claim 1, wherein the one or more sensors are disposed at a predetermined distance away from the subject, the predetermined distance being at least one decimeter.

4. The photoplethysmographic monitoring system of claim 1, wherein the at least two color channels are associated with a color model, the color model being based on a color model convention allocating respective wavelength portions to the at least two color channels, the color model is a color space based on a color space mapping convention, respective wavelength portions are assigned to respective axes of the color space, and the color space is an additive color space composed of three color channels.

5. The photoplethysmographic monitoring system of claim 1, wherein the one or more processors are further configured to determine:
(i) a level of bilirubin accumulated in the subject's dermis based on constant or quasi-constant channel signal strengths, and
(ii) an estimate of a serum bilirubin level compared to a skin-bilirubin level.

6. The photoplethysmographic monitoring system of claim 1, wherein the one or more processors are further configured to:
determine relative channel signal strength information indicative of impending suffocation.

7. The photoplethysmographic monitoring system of claim 6, wherein the one or more processors are further configured to:
(i) determine oxygenation information based on a ratio of the detected channel signal strengths, the oxygenation information being indicative of a ratio of hemoglobin and oxyhemoglobin in the subject's blood, and
(ii) output an alert signal responsive to the ratio exceeding a reference threshold.

8. The photoplethysmographic monitoring system of claim 1, wherein the one or more processors are further configured to:
detect at least one indicative skin portion of the subject based on the skin radiation information.

9. The photoplethysmographic monitoring system of claim 1, further comprising:

a treating radiation source configured to emit radiation in a particular wavelength range, wherein the treating radiation source is disposed such that the emitted radiation is directed to the subject, and the one or more processors are further configured to
control operation of the treating radiation source based on the determined blood composition-indicative information of the subject.

10. A method for extracting physiological information indicative of at least one health symptom from detected electromagnetic radiation with a photoplethysmographic monitoring system, the photoplethysmographic monitoring system comprising one or more sensors and one or more processors, the method comprising:
receiving, with the one or more sensors, skin radiation information of a subject, the skin radiation information including wavelength-dependent image information, wherein the wavelength-dependent image information is composed of at least two color channels representative of respective wavelength portions, and the wavelength-dependent image information comprises at least a pulsating signal component;

detecting, with the one or more processors, relative channel signal strength information for the at least two color channels, wherein the relative channel signal strength information corresponding to the at least two color channels is represented by color vectors, and wherein the color vectors are moved along a path between minima and maxima corresponding to the pulsating signal component;

comparing, with the one or more processors, the color vectors' path with a reference vector path, wherein the reference vector path is obtained by monitoring healthy subjects;

determining, with the one or more processors, blood composition-indicative information of the subject based on the comparison of the color vectors' path and the reference vector path; and determining, with the one or more processors, a level of serum bilirubin in the subject's circulating blood based on signal strength fluctuations.

11. The method of claim 10, further comprising:
(i) determining, with the one or more processors, a ratio of the at least two color channels;
(ii) comparing, with the one or more processors, the determined ratio with a reference ratio, the reference ratio obtained by monitoring the healthy subjects; and
(iii) determining, with the one or more processors, blood composition-indicative information based on the comparison of the determined ratio and the reference ratio.

12. The method of claim 10, wherein the one or more sensors are disposed at a predetermined distance away from the subject, the predetermined distance being at least one decimeter.

13. The method of claim 10, wherein the at least two color channels are associated with a color model, the color model being based on a color model convention allocating respective wavelength portions to the at least two color channels, the color model is a color space based on a color space mapping convention, respective wavelength portions are assigned to respective axes of the color space, and the color space is an additive color space composed of three color channels.

14. The method of claim 10, further comprising: determining, with the one or more processors, (i) a level of bilirubin accumulated in the subject's dermis based on constant or quasi-constant channel signal strengths, and (ii) (ii) an estimate of a serum bilirubin level compared to a skin-bilirubin level.

15. The method of claim 10, further comprising:

determining, with the one or more processors, relative channel signal strength information indicative of impending suffocation.

16. The method of claim 15, further comprising:

(i) determining, with the one or more processors, oxygenation information based on a ratio of the detected channel signal strengths, the oxygenation information being indicative of a ratio of hemoglobin and oxyhemoglobin in the subject's blood; and (ii) outputting an alert signal responsive to the ratio exceeding a reference threshold.

17. The method of claim 10, further comprising:

detecting, with the one or more processors, at least one indicative skin portion of the subject based on the skin radiation information.

18. The method of claim 10, further comprising:

(i) emitting, with a treating radiation source, radiation in a particular wavelength range, wherein the treating radiation source is disposed such that the emitted radiation is directed to the subject, and (ii) controlling, with the one or more processors, operation of the treating radiation source based on the determined blood composition-indicative information of the subject.

* * * * *